United States Patent [19]

Lesher et al.

[11] Patent Number: 4,560,691
[45] Date of Patent: Dec. 24, 1985

[54] 5-(PHENYL)-1,6-NAPHTHYRIDIN-2(1H)-ONES, THEIR CARDIOTONIC USE AND PREPARATION

[75] Inventors: George Y. Lesher, Schodack; Baldev Singh, East Greenbush, both of N.Y.

[73] Assignee: Sterling Drug Inc., New York, N.Y.

[21] Appl. No.: 630,810

[22] Filed: Jul. 13, 1984

[51] Int. Cl.[4] ................... A61K 31/44; C07D 213/50; C07D 213/46; C07D 471/04
[52] U.S. Cl. .................................. 514/300; 546/122; 546/298; 514/350
[58] Field of Search ............... 546/122, 298; 514/300, 514/350; 424/263, 256

[56] References Cited

U.S. PATENT DOCUMENTS 4,412,077 10/1983 Lesher et al. ...................... 546/298
4,415,580 11/1983 Lesher et al. ...................... 424/263

OTHER PUBLICATIONS

Robert Morrison and Robert Boyd, "Organic Chemistry", Second Ed., Allyn and Bacon, Inc., Boston (1966).
Calain A. Buehler and Donald E. Pearson, "Survey of Organic Syntheses", Wiley-Interscience, 1970.
Hawes et al., J. Het. Chem. 11 (2), 151–155 (1974).
Kato et al., [J. Heterocyclic Chem. 18, 603–606 (1981)].
Kato et al., [Chem. Pharm. Bull. 17, 2411–2416 (1969)].

Primary Examiner—Henry R. Jiles
Assistant Examiner—Barbara Cassatt
Attorney, Agent, or Firm—Robert K. Bair; B. Woodrow Wyatt; Paul E. Dupont

[57] ABSTRACT

1-R-5-Ar-1,6-naphthyridin-2(1H)-ones (I) or salts thereof, where R is hydrogen or methyl, and Ar is phenyl or phenyl substituted by methyl, ethyl, methoxy, ethoxy, hydroxy, amino, acetylamino, methanesulfonylamino, bromo, chloro, fluoro, cyano or carbamyl are useful as cardiotonic agents and corresponding compounds where Ar is nitrophenyl are useful as intermediates. Also shown as intermediates, are 5-(Ar—CO)-6-[2-(di-lower-alkylamino)-ethenyl]-2(1H)-pyridinones (II) or salts thereof, where Ar is phenyl or phenyl substituted by methyl, ethyl, methoxy, ethoxy, bromo, chloro, fluoro, cyano or nitro and 5-(Ar—CO)-6-methyl-2(1H)-pyridinones (III) where Ar is phenyl or phenyl substituted by methyl, ethyl, methoxy, ethoxy, bromo, chloro, fluoro, hydroxy, cyano or nitro; said compounds (III) where Ar is phenyl or hydroxyphenyl also are useful as cardiotonic agents. Processes for preparing the compounds of formulas I, II and III are shown.

31 Claims, No Drawings

5-(PHENYL)-1,6-NAPHTHYRIDIN-2(1H)-ONES, THEIR CARDIOTONIC USE AND PREPARATION

BACKGROUND OF THE INVENTION (a) Field of the Invention

This invention relates to 5-(phenyl)-1,6-naphthyridin-2(1H)-ones, their cardiotonic use and their preparation.

(b) Information Disclosure Statement

Hawes et al., J. Heterocyclic. Chem. 11 (2), 151–155 (1974), show the preparation of 3-phenyl-1,6-naphthridin-2(1H)-one and 3-(4-nitrophenyl)-1,6-naphthyridin-2(1H)-one by reacting 4-aminonicotinaldehyde with ethyl phenylacetate and ethyl 4-nitrophenylacetate, respectively. No utility is shown for either compound.

Lesher and Singh in U.S. Pat. No. 4,415,580, issued Nov. 15, 1983, shows as cardiotonic agents 5-(lower-alkyl)-1,6-naphthyridin-2(1H)-ones (I) and their preparation by reacting a 5-(lower-alkanoyl)-6-methyl-2(1H)-pyridinone with di-(lower-alkyl)formamide di-(lower-alkyl)acetal to produce 5-(lower-alkanoyl)-6-[2-(di-lower-alkylamino)ethenyl]-2(1H)-pyridinone (II) and reacting II with formamidine or ammonia or salt thereof to produce I.

Lesher and Singh in U.S. Pat. No. 4,412,077, issued Oct. 25, 1983, show as cardiotonic agents 5-(lower-alkanoyl)-6-(lower-alkyl)-2(1H)-pyridinones (I) and their preparation by reacting 2-(lower-alkanoyl)-1-(lower-alkyl)-ethenamine (II) with a lower-alkyl 2-propynoate.

Kato et al. [*J. Heterocyclic Chem.* 18, 603–606 (1981)] show, inter alia, the dehydrogenation of 5-acetyl-3,4-dihydro-6-methyl-2(1H)-pyridinone by heating it with palladium black to produce 5-acetyl-6-methyl-2(1H)-pyridinone, which in turn is reacted with phosphorus oxychloride (phosphoryl chloride) to produce a mixture of 6-chloro-3-ethynyl-2-methylpyridine and 6-chloro-3-(1-chlorovinyl)-2-methylpyridine.

Kato et al. [Chem. Pharm. Bull. 17, 2411–2416 (1969)] disclose the preparation of 5-acetyl-3,4-dihydro-6-methyl-2(1H)-pyridinone in two ways: (a) by refluxing 4-oxo-2-penten-2-amine and acrylic anhydride in chloroform (75% yield); and (b) by heating 4-oxo-2-penten-2-amine and ethyl acrylate in ethanol containing sodium ethoxide (9% yield).

SUMMARY OF THE INVENTION

In a composition of matter aspect the invention resides in 1-R-5-Ar-1,6-naphthyridin-2(1H)-one having the formula I

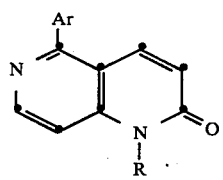

or acid-addition or cationic salt thereof, where R is hydrogen or methyl and Ar is phenyl or phenyl substituted by a member selected from methyl, ethyl, methoxy, ethoxy, hydroxy, amino, acetylamino, methanesulfonylamino, bromo, chloro, fluoro, nitro, cyano or carbamyl. These compounds of formula I other than those where Ar is phenyl substituted by nitro are useful as cardiotonic agents, as determined by standard pharmacological evaluation procedures. The compounds of formula I where Ar is phenyl substituted by nitro are useful as intermediates.

In another composition of matter aspect, the invention resides in 5-(Ar-CO)-6-[2-(di-lower-alkylamino)ethenyl]-2(1H)-pyridinone having the formula II

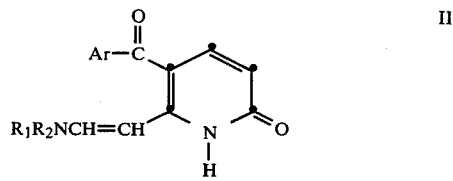

or acid-addition salt thereof, where Ar is phenyl or phenyl substituted by a member selected from methyl, ethyl, methoxy, ethoxy, bromo, chloro, fluoro, cyano or nitro, and $R_1$ and $R_2$ are each lower-alkyl. The compounds of formula II are useful as intermediates for preparing said above compounds having formula I.

Another composition of matter aspect of the invention resides in 5-(Ar—CO)-6-methyl-2(1H)-pyridinone having formula III

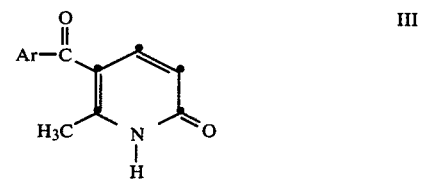

where Ar is phenyl and phenyl substituted by a member selected from methyl, ethyl, methoxy, ethoxy, bromo, fluoro, chloro, hydroxy, cyano or nitro. The compounds of formula III are useful as intermediates for preparing the compounds of formula II. Also, the compounds of formula III where Ar is phenyl or hydroxyphenyl are useful as cardiotonic agents, as determined by standard pharmacological evaluation procedures.

A composition aspect of the invention resides in the cardiotonic composition for increasing cardiac contractility which comprises a pharmaceutically acceptable carrier and, as the active component thereof, a cardiotonically effective amount of 1-R-5-Ar-1,6-naphthyridin-2(1H)-one having the formula I or pharmaceutically acceptable acid-addition or cationic salt thereof, where R is hydrogen or methyl and Ar is phenyl or phenyl substituted by a member selected from methyl, ethyl, methoxy, ethoxy, hydroxy, amino, acetylamino, methanesulfonylamino, bromo, chloro, fluoro, cyano or carbamyl.

A method aspect of the invention resides in the method for increasing cardiac contractility in a patient requiring such treatment which comprises administering orally or parenterally in a solid or liquid dosage form to such patient a cardiotonically effective amount of 1-R-5-Ar-1,6-naphthyridin-2(1H)-one having the formula I or pharmaceutically acceptable acid-addition or cationic salt thereof, where R is hydrogen or methyl and Ar is phenyl or phenyl substituted by a member selected from methyl, ethyl, methoxy, ethoxy, hydroxy, amino, acetylamino, methanesulfonylamino, bromo, chloro, fluoro, cyano or carbamyl.

Another composition aspect of the invention resides in the cardiotonic composition for increasing cardiac contractility which comprises a pharmaceutically acceptable carrier and, as the active component thereof, a cardiotonically effective amount of 5-benzoyl-6-methyl-2(1H)-pyridinone or 5-(4-hydroxybenzoyl)-6-methyl-2(1H)-pyridinone.

Another method aspect of the invention resides in the method for increasing cardiac contractility in a patient requiring such treatment which comprises administering orally or parenterally in a solid or liquid dosage form to such patient a cardiotonically effective amount of 5-benzoyl-6-methyl-2(1H)-pyridinone or 5-(4-hydroxybenzoyl)-6-methyl-2(1H)-pyridinone.

A process aspect of the invention resides in the process which comprises reacting 5-(Ar-CO)-6-methyl-2(1H)-pyridinone having formula III with di-(lower-alkyl)formamide di-(lower-alkyl)acetal or bis(dimethylamino)-t-butoxymethane to produce 5-(Ar-CO)-6-[2-(di-lower-alkylamino)ethenyl]-2(1H)-pyridinone having formula II above, where Ar has the meaning given for formula II.

Another process aspect of the invention resides in the process which comprises reacting 5-(Ar-CO)-6-[2-(di-lower-alkylamino)ethenyl]-2(1H)-pyridinone of formula II with formamidine or ammonia or salt thereof to produce 5-Ar-1,6-naphthyridin-2(1H)-one having formula I where R is hydrogen, and Ar is phenyl or phenyl substituted by a member selected from methyl, ethyl, methoxy, ethoxy, bromo, chloro, fluoro, cyano or nitro.

Other process aspects of the invention reside in the respective processes which comprise: converting the compound of formula I where Ar is methoxyphenyl or ethoxyphenyl to the corresponding compound where Ar is hydroxyphenyl; converting the compound of formula I where Ar is bromophenyl to the corresponding compound where Ar is cyanophenyl and then converting the compound where Ar is cyanophenyl to the corresponding compound where Ar is carbamylphenyl; converting the compound of formula I where Ar is nitrophenyl to the corresponding compound where Ar is aminophenyl, and then converting the compound where Ar is aminophenyl to the corresponding compound where Ar is acetylaminophenyl, methylsulfonylamino or hydroxyphenyl; or methylating the compound of formula I where R is hydrogen to produce the corresponding compound where R is methyl.

DETAILED DESCRIPTION INCLUSIVE OF PREFERRED EMBODIMENTS

Preferred compounds having formula I are those where R is hydrogen and Ar is phenyl, 4-hydroxyphenyl, 4-carbamylphenyl, 4-aminophenyl, 4-bromophenyl and 4-chlorophenyl. A particularly preferred species having formula I is the compound where R is hydrogen and Ar is phenyl.

Preferred compounds having formula II are those where $R_1$ and $R_2$ are each methyl and Ar is phenyl, 4-methoxyphenyl, 4-bromophenyl, 4-chlorophenyl and 4-nitrophenyl. A particularly preferred species having formula II is the compound where $R_1$ and $R_2$ are each methyl and Ar is phenyl.

Preferred compounds having formula III are those where Ar is phenyl, 4-methoxyphenyl, 4-bromophenyl, 4-chlorophenyl, 4-hydroxyphenyl and 4-nitrophenyl. A particularly preferred species having formula III is the compound where Ar is phenyl.

The term "lower-alkyl" as used herein, e.g., as the meaning of $R_1$ or $R_2$ in formula II means alkyl radicals having from 1 to 4 carbon atoms which can be arranged as straight or branched chains, illustrated by methyl, ethyl, n-propyl, isopropyl, n-butyl, sec.-butyl, tert.-butyl and isobutyl.

The compounds of formulas I and II are useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts of the compounds of formula I and the compounds of formula II include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base are not vitiated by side effects ascribable to the anions. Appropriate pharmaceutically acceptable salts within the scope of the invention are those derived from mineral acids such as hydrochloric acid, hydrobromic acid, sulfuric acid, phosphoric acid and sulfamic acid; and organic acid such as lactic acid, acetic acid, citric acid, tartaric acid, methanesulfonic acid, ethanesulfonic acid, benzenesulfonic acid, p-toluenesulfonic acid, cyclohexylsulfonic acid, quinic acid, and the like, giving the hydrochloride, hydrobromide, sulfate, phosphate, sulfamate, lactate, acetate, citrate, tartrate, methanesulfonate, ethanesulfonate, benzenesulfonate, p-toluenesulfonate, cyclohexylsulfamate and quinate, respectively.

The acid-addition salts of said basic compound of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution. The acid-addition salts of said basic compound of formula II are similarly prepared but under anhydrous conditions.

Although pharmaceutically acceptable salts of said basic compounds of formulas I and II are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

Other pharmaceutically acceptable salts of said compound of formula I are those cationic salts derived from strong inorganic or organic bases, e.g., sodium hydroxide, potassium hydroxide, trimethylammonium hydroxide, to produce the corresponding cationic salt, e.g., sodium, potassium, trimethylammonium salt, respectively.

The molecular structures of the compounds of formulas I, II and III were assigned on the basis of evidence provided by infrared, ultraviolet, nuclear magnetic resonance and mass spectra, by the correspondence of calculated and found values for the elemental analyses, and by their method of preparation.

The manner of making and using the instant invention will now be generally described so as to enable a person skilled in the art of pharmaceutical chemistry to make and use the same.

The reaction of 5-(Ar-CO)-6-methyl-2(1H)-pyridinone (III), with di-(lower-alkyl)formamide di-(lower-alkyl)-acetal or bis(dimethylamino)-t-butoxymethane to produce 5-(Ar—CO)-6-[2-(di-lower-alkylamio)ethenyl]-2(1H)-pyridinone (II) is carried out by heating the reactants at about 75° C. to 125° C., preferably about 90° C. to 110° C., and preferably in a suitable inert solvent. The reaction is preferably run by heating III with dimethylformamide dimethyl acetal in dimethylformamide on a steam bath or by refluxing III with bis(dimethylamino)-t-butoxymethane in dioxane (p-dioxane). The reaction of a compound of formula III where Ar is hydroxyphenyl results in the formation of a compound of formula II where Ar is methoxyphenyl.

The intermediate 5-(Ar—CO)-6-methyl-2(1H)-pyridin-one (III) is prepared by heating 1-methyl-3-oxo-3-Ar-1-propenamine with a lower-alkyl, preferably methyl or ethyl, 2-propynoate, preferably in a suitable solvent. The reaction is run at about 100° C. to 155° C., preferably in refluxing dimethylformamide.

The intermediate 1-methyl-3-oxo-3-Ar-1-propenamine is conveniently prepared by the generally known procedure of reacting 1-Ar-1,3-butanedione with aqueous ammonia in methanol at ambient temperature as illustrated hereinbelow.

The reaction of 5-(Ar—CO)-6-[2-(di-lower-alkylamino)ethenyl]-2(1H)-pyridinone (II) with a formamidine or ammonium salt, preferably acetate, to produce 5-Ar-1,6-naphthyridin-2(1H)-one (I where R is hydrogen) is carried out by heating the reactants at about 100° C. to 160° C., preferably about 155° C. to 160° C., in a suitable solvent, preferably dimethylformamide, other solvents being dioxane, n-butanol, n-hexanol, and the like. Preferred salts of formamidine and ammonia are those of weak organic or inorganic acids, for example, acetate, citrate, lactate, tartrate, carbonate, and the like, although salts of strong acids, e.g., hydrochloride and sulfate, also can be used. Optionally, the reaction can be run using ammonia under pressure.

The conversion of a compound of formula I where Ar is methoxyphenyl or ethoxyphenyl to the corresponding compound of formula I where Q is hydroxyphenyl is carried out by reacting said methoxyphenyl or ethoxyphenyl compound with a reagent capable of converting methoxyphenyl or ethoxyphenyl to hydroxyphenyl, e.g., hydrogen bromide, lithium iodide and collidine, and the like.

The conversion of a compound of formula I where Ar is bromophenyl to the corresponding compound of formula I where Ar is cyanophenyl is carried out by heating said bromophenyl compound with cuprous cyanide in an appropriate solvent, preferably in refluxing dimethylformamide.

The partial hydrolysis of a compound of formula I where Ar is cyanophenyl to produce a compound of formula I where Ar is carbamylphenyl is carried out preferably using concentrated sulfuric acid at about room temperature, i.e., about 20° C. to 30° C. Optionally, other strong inorganic acids, e.g., phosphoric acid, polyphosphoric acid, can be used in place of sulfuric acid.

The reduction of a compound of formula I where Ar is nitrophenyl to produce the corresponding compound of formula I where Ar is aminophenyl is carried out with an agent capable of reducing nitro to amino, either by catalytic hydrogenation using Pd/C, $PtO_2$ or Raney Ni catalyst or by chemical reduction, i.e., using reduced iron, zinc or iron and hydrochloric acid, stannous chloride and hydrochloric acid, and the like.

The conversion of a compound of formula I where Ar is aminophenyl to the corresponding compound where Ar is acetylamino or methanesulfonylamino is carried out by reacting said aminophenyl compound respectively with an acetylating agent, e.g., acetic anhydride or acetyl chloride, or with a methanesulfonylating agent, e.g., methanesulfonyl chloride.

The conversion of a compound of formula I where Ar is aminophenyl to the corresponding compound where Ar is hydroxyphenyl is carried out by converting the aminophenyl compound to its diazonium salt by reaction with nitrous acid in an ice bath and warming an aqueous solution of the latter to produce the hydroxyphenyl compound of formula I.

The methylation of a compound of formula I where R is hydrogen to produce the corresponding compound where R is methyl is carried out by reacting said compound (I) where R is hydrogen with a methylating agent, e.g., preferably by heating with methyl iodide or bromide in a suitable solvent, e.g., dimethylformamide, in the presence of an acid-acceptor, e.g., anhydrous potassium carbonate.

The following examples will further illustrate the invention without, however, limiting it thereto.

A. 5-(AR—CO)6-METHYL-2(1H)-PYRIDINONES

A-1. 5-Benzoyl-6-methyl-2(1H)-pyridinone

A mixture containing 200 ml of methanol, 50 ml of concentrated aqueous ammonium hydroxide and 50 g of 1-phenyl-1,3-butanedione (same as benzoylacetone) was stirred at ambient temperature for 22 hours after which time a tlc analysis (ether/silica gel) indicated very little remaining starting material. Some white solid 1-methyl-3-phenyl-3-oxo-1-propenamine had crystallized from the pale yellow solution. The mixture was concentrated on a rotary evaporator to dryness to yield 1-methyl-3-phenyl-3-oxo-1-propenamine as a yellow solid. To the yellow solid was added 75 ml of dimethylformamide and 25 g of methyl propiolate (same as methyl 2-propynoate) and the resulting mixture was refluxed for 10 hours, and concentrated on a rotary evaporator. The remaining solid was recrystallized from isopropyl alcohol and dried at 90°–95° C. to yield 29.6 g of 5-benzoyl-6-methyl-2(1H)-pyridinone, m.p. 185°–187° C. The mother liquor from the above recrystallization was concentrated on a rotary evaporator to yield another 6 g of the product.

A-2. 5-(4-Methoxybenzoyl)-6-methyl-2(1H)pyridinone

To a stirred solution containing 93 g of 3-(4-methoxyphenyl)-1-methyl-3-oxo-1-propenamine and 200 ml of dimethylformamide was added 46 ml of methyl propiolate over a 30 minute period and the reaction mixture was stirred at ambient temperature for 3 hours and then gently refluxed for 24 hours. The reaction mixture was allowed to cool, treated with 200 ml of isopropyl alcohol and the solid filtered. The solid was washed with isopropyl alcohol and dried at 90°–95° C. to yield, as white shiny crystals, 75.8 g of 5-(4-methoxybenzoyl)-6-methyl-2(1H)-pyridinone, m.p. 228°–230° C.

The intermediate 3-(4-methoxyphenyl)-1-methyl-3-oxo-1-propenamine was prepared as follows: A mixture containing 106 g of 1-(4-methoxyphenyl)-1,3-butanedione, 500 ml of methanol and 200 ml of concentrated aqueous ammonium hydroxide was allowed to stand at room temperature for 4 hours and then chilled in a refrigerator. The separated crystalline product was collected, washed with ether and dried at 90°–95° C. to yield 93.7 g of 3-(4-methoxyphenyl-1-methyl-3-oxo-1-propenamine, m.p. 126°–128° C.

A-3. 5-(4-Hydroxybenzoyl)-6-methyl-2(1H)-pyridinone

A mixture containing 13 g of 5-(4-methoxybenzoyl)-6-methyl-2(1H)-pyridinone and 100 ml of 48% aqueous hydrogen bromide solution was refluxed for 7 hours and then allowed to stand at room temperature overnight. The reaction mixture was concentrated to dryness on a rotary evaporator. To the residue was added 100 ml of water and the aqueous mixture was neutralized by adding aqueous ammonium hydroxide solution. The solid was collected, washed with water and air dried. The solid was recrystallized from 100 ml of ethanol and dried at 80°–85° C. to yield 11.4 g of 5-(4-hydroxybenzoyl)-6-methyl-2(1H)-pyridinone, m.p. 280°–282° C.

A-4. 5-(4-Bromobenzoyl)-6-methyl-2(1H)-pyridinone m.p. 251°–253° C., 50.2 g, was prepared following the procedure described in Example A-2 using 56 g of 3-(4-bromophenyl)-1-methyl-3-oxo-1-propenamine, 200 ml of dimethylformamide, 20.5 ml of methyl propiolate and refluxing the reaction mixture for 16 hours.

The intermediate 3-(4-bromophenyl)-1-methyl-3-oxo-1-propenamine, m.p. 126°–128° C., 56.8 g, was prepared following the procedure described in Example A-2 using 83 g of 1-(4-bromophenyl)-1,3-butanedione, 750 ml of methanol and 100 ml of concentrated aqueous ammonium hydroxide solution. The solid residue after stripping the reaction mixture to dryness on a rotary evaporator was treated with 500 ml of boiling n-hexane, the mixture allowed to stand at room temperature overnight, and, the product collected and dried at room temperature.

A-5. 5-(4-Chlorobenzoyl)-6-methyl-2(1H)-pyridinone m.p. 239°–240° C., 21.0 g, was prepared following the procedure described in Example A-2 using 3-(4-chlorophenyl)-1-methyl-3-oxo-1-propenamine, 19 ml of methyl propiolate and 250 ml of dimethylformamide. A second crop of 4.0 g of the product, m.p. 236°–238° C. was obtained.

The intermediate 3-(4-chlorophenyl)-1-methyl-3-oxo-1-propenamine, 30.1 g, m.p. 126°–130° C. was prepared by first chilling a mixture of 51.7 g of 1-(4-chlorophenyl)-1,3-butanedione and 450 ml of methanol, and passing anhydrous ammonia gas to the stirred mixture chilled in an ice bath for a period of about 50 minutes. The reaction vessel was stoppered and allowed to stand at room temperature for 24 hours. The mixture was then evaporated on a rotary evaporator and the remaining mixture slurried with n-hexane. The resulting solid was collected by filtration. The filtered product was again slurried with n-hexane, collected and dried in a vacuum oven at room temperature to yield said 3-(4-chlorophenyl)-1-methyl-3-oxo-1-propenamine.

A-6. 6-Methyl-5-(4-nitrobenzoyl)-2(1H)-pyridinone m.p. 282°–284° C., 5.0 g, was obtained following the procedure described in Example A-2 using 20 g of 3-(4-nitrophenyl)-1-methyl-3-oxo-1-propenamine, 9.5 ml of methyl propiolate and 100 ml of dimethylformamide.

3-(4-Nitrophenyl)-1-methyl-3-oxo-1-propenamine was prepared as follows: In a 2 liter round bottom flask adapted with a reflux condenser, drying tube and a water separator were added 1-(4-nitrophenyl)-1,3-butanedione, 97 g of ammonium acetate and 1 liter of toluene. The reaction mixture was refluxed with stirring for 5 and ½ hours and cooled. The separated solid was collected, washed with n-hexane and dried in a vacuum oven at 90° C. to produce 83.1 g of 3-(4-nitrophenyl)-1-methyl-3-oxo-1-propenamine, m.p. 176°–177° C.

A-7. 5-(4-Cyanobenzoyl)-6-methyl-2(1H)-pyridinones was prepared following the procedure described in Example A-2 using 24.3 g of 3-(4-cyanophenyl)-1-methyl-3-oxo-1-propenamine, 12.5 ml of methyl propiolate and 100 ml of dimethylformamide. After a refluxing period of 24 hours, the reaction mixture was cooled whereupon the product precipitated, was collected, washed with ethanol and dried in a vacuum oven at 90° C. There was thus obtained 12.2 g of product, m.p. 267°–269° C., which was recrystallized from dimethylformamide using decolorizing charcoal, washed with ethanol and dried in a vacuum oven at 90° C. to yield 7.4 g of 5-(4-cyanobenzoyl)-6-methyl-2(1H)-pyridinone, m.p. 268°–270° C.

3-(4-Cyanophenyl)-1-methyl-3-oxo-1-propenamine, m.p. 172°–175° C., 29.1 g, was prepared following the procedure described in Example A-5 using 33.2 g of 1-(4-cyanophenyl)-1,3-butanedione, 37.25 g of ammonium acetate and 300 ml of toluene.

Following the procedure described in Example A-1 but using in place of 1-phenyl-1,3-butanedione a molar equivalent quantity of the appropriate 1-Ar-1,3-butanedione to form first the corresponding 1-methyl-3-Ar-3-oxo-1-propenamine which is then reacted with methyl propiolate, it is contemplated that the 5-(Ar—CO)-6-methyl-2(1H)-pyridinones of Examples A-8 through A-11 can be obtained.

A-8. 5-(4-Methylbenzoyl)-6-methyl-2(1H)-pyridinone first using 1-(4-methylphenyl)-1,3-butanedione to prepare 3-(4-methylphenyl)-1-methyl-3-oxo-1-propenamine.

A-9. 5-(4-Ethylbenzoyl)-6-methyl-2(1H)-pyridinone first using 1-(4-ethylphenyl)-1,3-butanedione to produce 3-(4-ethylphenyl)-1-methyl-3-oxo-1-propenamine.

A-10. 5-(4-Ethoxybenzoyl)-6-methyl-2(1H)-pyridinone first using 1-(4-ethoxyphenyl)-1,3-butanedione to produce 3-(4-ethoxyphenyl)-1-methyl-3-oxo-1-propenamine.

A-11. 5-(4-Fluorobenzoyl)-6-methyl-2(1H)-pyridinone first using 1-(4-fluorophenyl)-1,3-butanedione to produce 3-(4-fluorophenyl)-1-methyl-3-oxo-1-propenamine.

B.
5-(Ar—CO)-6-[2-(DI-LOWER-ALKYLAMINO)ETHENYL]-2(1H)-PYRIDINONES

B-1.
5-Benzoyl-6-[2-(dimethylamino)ethenyl]-2(1H)-pyridinone

A mixture containing 26.5 g of 5benzoyl-6-methyl-2(1H)-pyridinone, 100 ml of dimethylformamide and 21 ml of dimethylformamide dimethyl acetal was heated on a steam bath with stirring for 8 hours and then concentrated on a rotary evaporator to yield a solid residue. The residue was recrystallized from methanol and dried in a vacuum oven at 80°–85° C., to yield 15.8 g of 5- benzoyl-6-[2-(dimethylamino)ethenyl]-2(1H)-pyridinone, m.p. 202°–204° C.

Acid-addition salts of 5-benzoyl-6-[2-(dimethylamino)ethenyl]-2(1H)-pyridinone are conveniently prepared by adding to a mixture of 2 g of 5-benzoyl-6-[2-(dimethylamino)ethenyl]-2(1H)-pyridinone in about 40 ml of methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 5-benzoyl-6-[2-(dimethylamino)ethenyl]-2(1H)-pyridione and the appropriate acid, e.g., lactic acid or hydrochloric acid, to prepare respectively the monolactate or monohydrochloride in aqueous solution.

B-2.
6-[2-(Dimethylamino)ethenyl]-5-(4-methoxybenzoyl)-2(1H)-pyridinone

A mixture containing 50 g of 5-(4-methoxybenzoyl)-6-methyl-2(1H)-pyridinone, 400 ml of p-dioxane and 40 ml of bis(dimethyamino)-t-butoxymethane was refluxed with stirring for 5 and ½ hours. The reaction mixture was allowed to cool and the separated crystalline product was collected, washed with ethanol and dried in a vacuum oven at 80°–85° C., to yield 65.8 g of 6-[2-(dimethylamino)ethenyl]-5-(4-methoxybenzoyl)-2(1H)-pyridinone, m.p. 216°–218° C.

Acid-addition salts of 6-[2-(dimethylamino)ethenyl]-5-(4-methoxybenzoyl)-2(1H)-pyridinone are prepared following the procedure described in Example B-1.

B-3.
5-(4-Bromobenzoyl)-6-[2-(dimethylamino)ethenyl]-2(1H)-pyridinone m.p. 265°–268° C. with decomposition, 53.8 g, was prepared following the procedure described in Example B-2 using 44 g of 5-(4-bromobenzoyl)-6-methyl-2(1H)-pyridinone, 300 ml of p-dioxane and 35 ml of bis-(dimethylamino)-t-butoxymethane.

B-4.
5-(4-Chlorobenzoyl)-6-[2-(dimethylamino)-ethenyl]-2(1H)-pyridinone m.p. 263°–263.5° C., 6.75 g, was prepared following the procedure described in Example B-1 using 9.3 g of 5-(4-chlorobenzoyl)-2-methyl-2(1H)-pyridinone, 5.53 ml of dimethylformamide dimethyl acetal and 120 ml of p-dioxane as the solvent.

B-5.
6-[2-(Dimethylamino)ethenyl]-5-(4-nitrobenzoyl)-2(1H)-pyridinone m.p. 304°–305° C., 53.7 g, was prepared following the procedure described in Example B-2 using 46.0 g of 6-methyl-5-(4-nitrobenzoyl)-2(1H)-pyridionone, 41.7 g of bis(dimethylamino)-t-butoxymethane, 300 ml of p-dioxane and a reflux period of 2 hours.

Following the procedure described in Example B-1 but using in place of 5-benzoyl-6-methyl-2(1H)-pyridinone a molar equivalent quantity of the appropriate 5-(Ar—CO)-6-methyl-2(1H)-pyridinone, it is contemplated that there can be obtained the corresponding 5-(Ar—CO)-6-[2-(dimethylamino)ethenyl]-2(1H)-pyridones of Examples B-6 through B-10.

B-6.
5-(4-Cyanobenzoyl)-6-[2-(dimethylamino)ethenyl]-2(1H)-pyridinone using 5-(4-cyanobenzoyl)-6-methyl-2(1H)-pyridinone.

B-7.
6-[2-(Dimethylamino)ethenyl]-5-(4-methylbenzoyl)-2(1H)-pyridinone using 6-methyl-5-(4-methylbenzoyl)-2(1H)-pyridinone.

B-8.
5-(4-Ethylbenzoyl)-6-[2-(dimethylamino)ethenyl]-2(1H)-pyridinone using 5-(4-ethylbenzoyl)-6-methyl-2(1H)-pyridinone.

B-9.
5-(4-Ethoxybenzoyl)-6-[2-(dimethylamino)ethenyl]-2(1H)-pyridinone using 5-(4-ethoxybenzoyl)-6-methyl-2(1H)pyridinone.

B-10.
5-(4-Fluorobenzoyl)-6-[2-(dimethylamino)ethenyl]-2(1H)-pyridinone using 5-(4-fluorobenzoyl)-6-methyl-2(1H)-pyridinone.

C. 5-AR-1,6-NAPHTHYRIDIN-2(1H)-ONES

C-1. 5-Phenyl-1,6-naphthyridin-2(1H)-one

A mixture containing 13.4 g of 5-benzoyl-6-[2-(dimethylamino)ethenyl]-2(1H)-pyridinone, 100 ml of dimethylformamide and 12 g of ammonium acetate was heated with stirring on a steam bath for 7 hours and then concentrated on a rotary evaporator. The remaining solid residue was treated with 100 ml of water, the mixture filtered, the collected solid air-dried, recrystallized from ethanol and dried in a vacuum oven at 90°–95° C. to yield 6.3 g of 5-phenyl-1,6-naphthyridin-2(1H)-one, m.p. 261°–263° C.

Acid-addition salts of 5-phenyl-1,6-naphthyridin-2(1H)-one are conveniently prepared by adding to a mixture of 2 g of 5-phenyl-1,6-naphthyridin-2(1H)-one in about 40 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitate, e.g., dimethanesulfonate, sulfate, phosphate, respectively. Also, the acid-addition salt is conveniently prepared in aqueous solution by adding to water with stirring molar equivalent quantities each of 5-phenyl-1,6-naphthyridin-2(1H)-one and the appropriate acid, e.g., lactic acid or hydrochloric acid, to prepare respectively the monolactate or monohydochloride salt in aqueous solution.

Cationic salts of 5-phenyl-1,6-naphthyridin-2(1H)-one are conveniently prepared by reaction with an equivalent quantity of the appropriate base, for example, sodium hydroxide, potassium hydroxide or trimethylammonium hydroxide, to produce the corresponding respective sodium, potassium or trimethylammonium salt.

C-2. 5-(4-Methoxyphenyl)-1,6-naphthyridin-2(1H)-one m.p. 250°–252° C., 42.8 g, was prepared following the procedure described in Example C-1 using 54 g of 6-[2-(dimethylamino)ethenyl]-5-(4-methoxybenzoyl)-2(1H)-pyridinone, 400 ml of dimethylformamide, 30.8 g of ammonium acetate, a refluxing period of 5 hours and recrystallization from methanol.

C-3. 5-(4-Hydroxyphenyl)-1,6-naphthyridin-2(1H)-one

A mixture containing 12.6 g of 5-(4-methoxyphenyl)-1,6-naphthyridin-2(1H)-one and 100 ml of 40% aqueous hydrogen bromide was refluxed for 14 hours, cooled and evaporated on a rotary evaporator. The remaining solution was neutralized by adding aqueous ammonium hydroxide solution. The resulting yellow solid was collected, washed with water, dried, recrystallized from dimethylformamide and dried in a vacuum oven at 90°–95° C. to yield 11.2 g of 5-(4-hydroxyphenyl)-1,6-naphthyridin-2(1H)-one, m.p. >300° C.

Acid-addition salts of 5-(4-hydroxyphenyl)-1,6-naphthyridin-2(1H)-one are conveniently prepared following the procedure described for preparing the corresponding acid-addition salts in Example C-1.

C-4. 5-(4-Bromophenyl)-1,6-naphthyridin-2(1H)-one m.p. 278°–280° C., 40.4 g, was prepared following the procedure described in Example C-1 using 47 g of 5-(4-bromobenzoyl)-6-[2-(dimethylamino)ethenyl]-2(1H)-pyridinone, 300 ml of dimethylformamide and 21 g of ammonium acetate. The product was obtained after evaporation of the reaction mixture by washing the pulverized residue with ethanol and drying it in a vacuum oven at 90°–95° C.

C-5. 5-(4-Cyanophenyl)-1,6-naphthyridin-2(1H)-one

A mixture containing 15 g of 5-(4-bromophenyl)-1,6-naphthyridin-2(1H)-one, 300 ml of dimethylformamide and 8.6 g of cuprous cyanide was refluxed with stirring for 96 hours, cooled and stripped to dryness using a rotary evaporator. To the residue was added 300 ml of concentrated aqueous ammonium hydroxide solution and 20 ml of glacial acidic acid. The resulting mixture was chilled in ice, next treated with 71 ml of (5.25% aqueous sodium hypochlorite solution, then stirred in an ice bath for 3 hours and allowed to stand at room temperature for 4 hours. The brown solid was collected, washed with water, dried, dissolved in 300 ml of boiling dimethylformamide, the hot solution treated with decolorizing charcoal and filtered, and the filtrate concentrated to dryness. The residue was recrystallized from dimethylformamide to produce 8.6 g of 5-(4-cyanophenyl)-1,6-naphthyridin-2(1H)-one, m.p. >300° C.

Following the procedure described in Example C-1 using in place of 5-benzoyl-6-[2-(dimethylamino)ethenyl]-2(1H)-pyridinone a molar equivalent quantity of 5-(4-cyanobenzoyl)-6-[2-(dimethylamino)ethenyl]-2(1H)-pyridinone, it is contemplated that there can be obtained 5-(4-cyanophenyl)-1,6-naphthyridin-2(1H)-one.

C-6. 5-(4-Carbamylphenyl)-1,6-naphthyridin-2(1H)-one

To a 35 ml of concentrated sulfuric acid chilled in an ice bath was added 5 g of 5-(4-cyanophenyl)-1,6-naphthyridin-2(1H)-one. The resulting mixture was allowed to stand in an ice bath for 30 minutes and then at room temperature overnight. The mixture was poured onto ice and neutralized by adding aqueous ammonium hydroxide solution. The resulting white precipitate was collected, washed with distilled water, dried in a vacuum oven at 90°–95° C. to yield 4.8 g of 5-(4-carbamylphenyl)-1,6-naphthyridin-2(1H)-one, m.p. >300° C.

Acid-addition salts of 5-(4-carbamylphenyl)-1,6-naphthyridin-2(1H)-one are conveniently prepared as described above in Example C-1.

C-7. 5-(4-Chlorophenyl)-1,6-naphthyridin-2(1H)-one m.p. 282°–284° C., 9.50 g, was prepared following the procedure described in Example C-1 using 12.8 g of 5-(4-chlorobenzoyl)-6-[2-(dimethylamino)ethenyl]-2(1H)-pyridinone, 4.53 g of ammonium acetate, 200 ml of dimethylformamide and a reflux period of 8 hours.

C-8. 5-(4-Nitrophenyl)-1,6-naphthyridin-2(1H)-one m.p. >300° C., 39.1 g, was prepared following the procedure described in Example C-1 using 47.5 g of 6-[2-(dimethylamino)ethenyl]-5-(4-nitrobenzoyl)-2(1H)-pyridinone, 24.2 g of ammonium acetate, 250 ml of dimethylformamide and a reflux period of 4 hours.

C-9. 5-(4-Aminophenyl)-1,6-naphthyridin-2(1H)-one

A mixture containing 10.68 g of 5-(4-nitrophenyl)-1,6-naphthyridin-2(1H)-one, 1 g of platinum oxide and 300 ml of acetic acid was catalytically hydrogenated in a Paar hydrogenator at room temperature over a period of about 1 hour. The catalyst was filtered off and the filtrate was concentrated on a rotary evaporator. The residue was slurried in boiling methanol, the mixture filtered, and the collected solid washed with methanol and dried in a vacuum oven at about 90° C. The solid was then recrystallized using 100 ml of boiling dimethylformamide and decolorizing charcoal, filtering the hot mixture, and concentrating the filtrate on a rotary evaporator. The remaining solid was slurried with methanol, the mixture filtered and the collected solid dried in a vacuum oven at 90° C. to yield 5.2 g of 5-(4-aminophenyl)-1,6-naphthyridin-2(1H)-one, m.p. 309°–312° C.

C-10. 5-(3-Nitrophenyl)-1,6-naphthyridin-2(1H)-one

To a mixture containing 16.7 g of 5-phenyl-1,6-naphthyridin-2(1H)-one and 250 ml of concentrated sulfuric acid was added portionwise 7.6 g of potassium nitrate with stirring, keeping the mixture in an ice bath. The addition was completed within 15 minutes and the temperature of the reaction mixture was kept below 10° C. during addition. The reaction mixture was then stirred in the ice bath for 40 minutes, allowed to warm up to room temperature and then stirred at room temperature for 5 and ½ hours. The reaction mixture was poured over ice and the resulting mixture was made basic using concentrated ammonium hydroxide solution. The mixture was made slightly acidic using glacial acetic acid and chilled. The separated solid was collected and dried. The solid was recrystallized from boiling dimethylformamide using decolorizing charcoal, the hot mixture filtered and the filtrate chilled. The separated solid was collected, washed with ethanol and dried in a vacuum oven at 90° C. to yield 12.2 g of 5-(3-nitrophenyl)-1,6-naphthyridin-2(1H)-one, m.p. >300° C.

C-11. 5-(3-Amino)-1,6-naphthyridin-2(1H)-one

To a stirred mixture containing 60.34 g of stannous chloride in a mixture of 200 ml of concentrated hydrochloric acid and 250 ml of ethanol was added over a 10 minute period 23.8 g of 5-(3-nitrophenyl)-1,6-naphthyridin-2(1H)-one and the resulting reaction mixture was heated to reflux for 6 hours and cooled. The separated solid was collected, washed with concentrated hydrochloric acid and dried in a vacuum oven at 90° C. to yield 26.2 g of 5-(3-amino)-1,6-naphthyridin-2(1H)-one as its dihydrochloride monohydrate, m.p. >300° C.

C-12.
5-(3-Acetylaminophenyl)-1,6-naphthyridin-2(1H)-one

To a stirred mixture containing 6.57 g of 5-(3-aminophenyl)-1,6-naphthyridin-2(1H)-one dihydrochloride monohydrate and 63 ml of pyridine was added dropwise over a period of 5 minutes 4.8 ml of acetic anhydride. The resulting mixture was stirred at room temperature overnight. The reaction mixture was concentrated on a rotary evaporator to dryness. The residue was slurried with water; and, the solid was collected, washed with water and dried in a vacuum oven at 90° C. to yield 5.4 g of 5-(3-acetylaminophenyl)-1,6-naphthyridin-2(1H)-one monohydrate, m.p. 258°–262° C.

C-13.
5-(3-Methanesulfonylaminophenyl)-1,6-naphthyridin-2(1H)-one

To a mixture containing 6.57 g of 5-(3-aminophenyl)-1,6-naphthyridin-2(1H)-one dihydrochloride monohydrate and 64 ml of pyridine was added dropwise with stirring 2.9 ml of methanesulfonyl chloride and the reaction mixture was stirred for about 30 minutes. The reaction mixture was concentrated on a rotary evaporator and to the residual oily material was added water whereupon a solid separated and then dissolved. To the solution was added about 10 ml of acetic acid and the mixture allowed to stand overnight. The solution was concentrated on a rotary evaporator and to the residue was added ethanol whereupon on standing crystallization resulted. The crystalline material was collected, washed with ethanol and dried in a vacuum oven at 90° C. to yield 6.0 g of 5-(3-methanesulfonylaminophenyl)-1,6-naphthyridin-2(1H)-one monohydrochloride, m.p. 258° C. with decomposition.

C-14. 5-(3-Hydroxyphenyl)-1,6-naphthyridin-2(1H)-one

To a stirred mixture containing 6.9 g of 5-(3-aminophenyl)-1,6-naphthyridin-2(1H)-one dihydrochloride monohydrate and 50 ml of water in an ice bath was slowly added 50 ml of concentrated sulfuric acid followed by 1.45 g of sodium nitrite. The reaction mixture was stirred in an ice bath for about 2 hours and then allowed to warm up to room temperature. It was next heated on a steam bath for about 2 hours and then allowed to stand at room temperature overnight. The reaction mixture was treated with ammonium hydroxide solution until it became weakly basic. The separated solid was collected, washed with water and dried in a vacuum oven at 90° C. The solid was recrystallized from boiling isopropyl alcohol using decolorizing charcoal, the mixture filtered and the filtrate concentrated until the solid separated. The solid was collected and washed with isopropyl alcohol. Additional solid was obtained by concentrating the filtrate. The solids were combined and recrystallized from dimethylformamide using decolorizing charcoal and dried in a vacuum oven at 90° C. to yield 1.3 g of 5-(3-hydroxyphenyl)-1,6-naphthyridin-2(1H)-one, m.p. 297°–299° C. with decomposition.

C-15. 1-Methyl-5-phenyl-1,6-naphthyridin-2(1H)-one

A mixture containing 22.2 g of 5-phenyl-1,6-naphthyridin-2(1H)-one, 13.18 g of anhydrous potassium carbonate and 300 ml of dimethylformamide was heated with stirring on a steam bath for 1 hour and to this mixture was added 6.9 g of methyl iodide. The resultig mixture was heated with stirring for an additional 6 hours, allowed to cool and the solvent removed by distillation under reduced pressure. To the residue was added 100 ml of 20% acetic acid and the resulting pale yellow solid was collected, washed with water, dried, recrystallized from methanol and dried at 90° C. to yield 16.4 g of 1-methyl-5-phenyl-1,6-naphthyridin-2(1H)-one, m.p. 190°–192° C.

Following the procedure described in Example C-1 but using in place of 5-benzoyl-6-[2-(dimethylamino)ethenyl]-2(1H)-pyridinone a molar equivalent quantity of the appropriate 5-(Ar—CO)-6-[2-(dimethylamino)ethenyl]-2(1H)-pyridinone, it is contemplated that there can be obtained the corresponding 5-Ar-1,6-naphthyridin-2(1H)-ones of Examples C-16 through C-20.

C-16. 5-(4-Cyanophenyl)-1,6-naphthyridin-2(1H)-one using 5-(4-cyanobenzoyl)-6-[2-(dimethylamino)ethenyl]-2(1H)-pyridinone.

C-17. 5-(4-Methylphenyl)-1,6-naphthyridin-2(1H)-one using 6-[2-(dimethylamino)ethenyl]-5-(4-methylbenzoyl)-2(1H)-pyridinone.

C-18. 5-(4-Ethylphenyl)-1,6-naphthyridin-2(1H)-one using 5-(4-ethylbenzoyl)-6-[2-(dimethylamino)ethenyl]-2(1H)-pyridinone.

C-19. 5-(4-Ethoxyphenyl)-1,6-naphthyridin-2(1H)-one using 5-(4-ethoxybenzoyl)-6-[2-(dimethylamino)ethenyl]-2(1H)-pyridinone.

C-20. 5-(4-Fluorophenyl)-1,6-naphthyridin-2(1H)-one using 5-(4-fluorobenzoyl)-6-[2-(dimethylamino)ethenyl]-2(1H)-pyridinone.

C-21. 5-(4-Hydroxyphenyl)-1,6-naphthridin-2(1H)-one

Following the procedure described in Example C-3 but using in place of 5-(4-methoxyphenyl)-1,6-napthridin-2(1H)-one a corresponding molar equivalent quantity of 5-(4-ethoxyphenyl)-1,6-naphthyridin-2(1H)-one, it is contemplated that 5-(4-hydroxyphenyl)-1,6-naphthyridin-2(1H)-one can be obtained.

The usefulness of the compounds of formula I (all but where Ar is phenyl substituted by nitro) and the compounds of formula III where Ar is phenyl or 4-hydroxyphenyl as cardiotonic agents is demonstrated by their effectiveness in standard pharmacological test procedures, for example, in causing a significant increase in contractile force of the isolated cat or guinea pig atria and papillary muscle and/or in causing a significant increase in cardiac contractile force in the anesthetized dog with lower or minimal changes in heart rate and blood pressure. Detailed descriptions of these test procedures appear in U.S. Pat. No. 4,072,746, issued Feb. 7, 1980.

Cardiotonic activity in said isolated cat or guinea pig atria and papillary muscle procedure is indicated by a significant increase, that is, greater than 25% (cat) or 30% (g.pig) in papillary muscle force and a significant increase, that is, greater than 25% (cat) or 30% (g.pig) in right atrial force, with a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force (PMF) or right atrial force (RAF) increase of 31% or greater. Representative examples of the compounds of Formulas I and III were tested by said guinea pig atria and papillary muscle procedure with the following results:

| Example | Dose µg/ml | % Change from Control RAF[a] | PMF |
|---|---|---|---|
| C-1 | 3 | 84 | 45 |
|  | 10 | 118 | 80 |
| C-2 | 10 | 16 | 56 |
|  | 30 | −19 | 71 |
| C-3 | 10 | 57 | 52 |
|  | 30 | 91 | 42 |
|  | 100 | 291 | 101 |
| C-4 | 10 | −49 | 43 |
|  | 30 | −79 | 51 |
| C-5 | 30 | 47 | 48 |
| C-6 | 3 | 71 | 58 |
|  | 30 | 48 | 137 |
| C-7 | 10 | −13 | 47 |
|  | 30 | −66 | 40 |
| C-9 | 1 | 50 | 39 |
|  | 3 | 132 | 98 |
|  | 10 | 52 | 128 |
| C-11 | 10 | 50 | 67 |
|  | 30 | 67 | 76 |
|  | 100 | 77 | 85 |
| C-13 | 30 | 77 | 52 |
| C-14 | 10 | 35 | 51 |
|  | 30 | 63 | 68 |
|  | 100 | 136 | 76 |
| C-15 | 100 | 35 | 76 |
| A-1 | 30 | 40 | 48 |
|  | 100 | 114 | 89 |
| A-3 | 100 | 80 | 66 |

[a] — sign before some values indicates percentage decrease of right atrial force.

When tested by said anesthetized dog procedure, the said cardiotonically active compounds of formula I at doses of 0.10, 0.30 and/or 1.0 mg/kg administered intravenously were found to cause significant increases, that is, 25% or greater, in cardiac contractile force or cardiac contractility with lower changes in heart rate and blood pressure. For example, when tested at said dose levels by this procedure, the compound of Examples C-1 was found to cause increases of about 42% to 153% in contractile force and lower changes in heart rate and blood pressure.

The present invention includes within its scope a cardiotonic composition for increasing cardiac contractility, said composition comprising a pharmaceutically acceptable carrier and, as the active component thereof, the compound of formula I (except where Ar is nitrophenyl) pharmaceutically acceptable or acid-addition or cationic salt thereof or the compound of formula III where Ar is phenyl or hydroxyphenyl. The invention also includes within its scope the method for increasing cardiac contractility in a patient requiring such treatment which comprises administering to such patient a cardiotonically effective amount of said cardiotonically active compound of formula I or formula III. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 1-R-5-Ar-1,6-naphthyridin-2(1H)-one having the formula

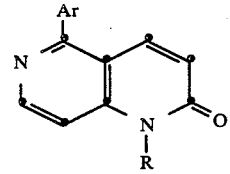

or acid-addition or cationic salt thereof, where R is hydrogen or methyl and Ar is phenyl or phenyl substituted by a member selected from methyl, ethyl, methoxy, ethoxy, hydroxy, amino, acetylamino, methanesulfonylamino, bromo, chloro, fluoro, nitro, cyano or carbamyl.

2. A compound according to claim 1 where R is hydrogen and Ar is phenyl, 4-hydroxyphenyl, 4-carbamylphenyl, 4-aminophenyl, 4-bromophenyl or 4-chlorophenyl.

3. 5-Phenyl-1,6-naphthyridin-2(1H)-one according to claim 1.

4. 5-(4-Hydroxyphenyl)-1,6-naphthyridin-2(1H)-one according to claim 1.

5. 5-(4-Carbamylphenyl)-1,6-naphthyridin-2(1H)-one according to claim 1.

6. 5-(4-Aminophenyl)-1,6-naphthyridin-2(1H)-one according to claim 1.

7. 5-(4-Bromophenyl)-1,6-naphthyridin-2(1H)-one according to claim 1.

8. 5-(4-Chlorophenyl)-1,6-naphthyridin-2(1H)-one according to claim 1.

9. 5-(Ar—CO)-6-[2-(di-lower-alkylamino)ethenyl]-2(1H)-pyridinone having the formula

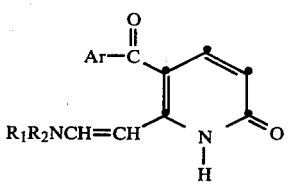

or acid-addition salt thereof, where Ar is phenyl or phenyl substituted by a member selected from methyl, ethyl, methoxy, ethoxy, bromo, chloro, fluoro, cyano or nitro, and $R_1$ and $R_2$ are each lower-alkyl.

10. A compound according to claim 9 where $R_1$ and $R_2$ are each methyl and Ar is phenyl, 4-methoxyphenyl, 4-bromophenyl, 4-chlorophenyl or 4-nitrophenyl.

11. 5-Benzoyl-6-(2-dimethylaminoethenyl)-2(1H)-pyridinone according to claim 9.

12. 6-(2-Dimethylaminoethenyl)-5-(4-methoxybenzoyl)-2(1H)-pyridinone according to claim 9.

13. 5-(4-Bromobenzoyl)-6-(2-dimethylaminoethenyl)-2(1H)-pyridinone according to claim 9.

14. 5-(4-Chlorobenzoyl)-6-(2-dimethylaminoethenyl)-2(1H)-pyridinone according to claim 9.

15. 6-(2-Dimethylaminoethenyl)-5-(4-nitrobenzoyl)-2(1H)pyridinone according to claim 9.

16. 5-(Ar—CO)-6-methyl-2(1H)-pyridinone having the formula

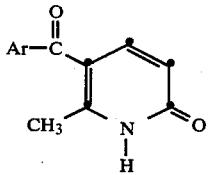

where Ar is phenyl or phenyl substituted by a member selected from methyl, ethyl, methoxy, ethoxy, bromo, chloro, fluoro, hydroxy, cyano or nitro.

17. A compound according to claim 16 where Ar is phenyl, 4-methoxyphenyl, 4-bromophenyl, 4-chlorophenyl, 4-hydroxyphenyl or 4-nitrophenyl.

18. 5-Benzoyl-6-methyl-2(1H)-pyridinone according to claim 16.

19. 5-(4-Methoxybenzoyl)-6-methyl-2(1H)-pyridinone according to claim 16.

20. 5-(4-Bromobenzoyl)-6-methyl-2(1H)-pyridinone according to claim 16.

21. 5-(4-Chlorobenzoyl)-6-methyl-2(1H)-pyridinone according to claim 16.

22. 6-Methyl-5-(4-nitrobenzoyl)-2(1H)-pyridinone according to claim 16.

23. 5-(4-Hydroxybenzyol)-6-methyl-2(1H)-pyridinone according to claim 16.

24. A cardiotonic composition for increasing cardiac contractility which comprises a pharmaceutically acceptable carrier and, as the active component thereof, a cardiotonically effective amount of the 1-R-5-Ar-1,6-naphthyridin-2(1H)-one of claim 1 or pharmaceutically acceptable acid-addition or cationic salt thereof, where R is hydrogen or methyl and Ar is phenyl or phenyl substituted by a member selected from methyl, ethyl, methoxy, ethoxy, hydroxy, amino, acetylamino, methanesulfonylamino, bromo, chloro, fluoro, cyano or carbamyl.

25. A cardiotonic composition according to claim 24 where in the active component R is hydrogen and Ar is phenyl, 4-hydroxyphenyl, 4-carbamylphenyl, 4-aminophenyl, 4-bromophenyl or 4-chlorophenyl.

26. A cardiotonic composition according to claim 24 where the active component is 5-phenyl-1,6-naphthyridine-2(1H)-one.

27. A method for increasing cardiac contractility in a patient requiring such treatment which comprises administering orally or parenterally in a solid or liquid dosage form to such patient a cardiotonically effective amount of the 1-R-5-Ar-1,6-naphthyridin-2(1H)-one of claim 1 or pharmaceutically acceptable acid-addition or cationic salt thereof, where R is hydrogen or methyl and Ar is phenyl or phenyl substituted by a member selected from methyl, ethyl, methoxy, ethoxy, hydroxy, amino, acetylamino, methanesulfonylamino, bromo, chloro, fluoro, cyano or carbamyl.

28. A method according to claim 27 where in the active component R is hydrogen and Ar is phenyl, 4-hydroxyphenyl, 4-carbamylphenyl, 4-aminophenyl, 4-bromophenyl or 4-chlorophenyl.

29. A method according to claim 27 where the active component is 5-phenyl-1,6-naphthyridin-2(1H)-one.

30. A cardiotonic composition for increasing cardiac contractility which comprises a pharmaceutically acceptable carrier and, as the active component thereof, a cardiotonically effective amount of 5-benzoyl-6-methyl-2(1H)-pyridinone or 5-(4-hydroxybenzoyl)-6-methyl-2(1H)-pyridinone according to claim 16.

31. A method for increasing cardiac contractility in a patient requiring such treatment which comprises administering orally or parenterally in a solid or liquid dosage form to such patient a cardiotonically effective amount of 5-benzoyl-6-methyl-2(1H)-pyridinone or 5-(4-hydroxyphenyl)-6-methyl-2(1H)-pyridinone of claim 16.

* * * * *

Disclaimer and Dedication 4,560,691.—*George Y. Lesher*, Schodack; *Baldev Singh*, East Greenbush, both of N. Y. 5-(PHENYL)-1, 6-NAPHTHYRIDIN-2(1H)-ONES, THEIR CARDIOTONIC USE AND PREPARATION. Patent dated Dec. 24, 1985. Disclaimer and Dedication filed Sept. 18, 1989, by the assignee, Sterling Drug Inc.

Hereby disclaims and dedicates to the Public claims 16, 17 and 22 of said patent.
[*Official Gazette October 31, 1989*]